(12) United States Patent
Jang et al.

(10) Patent No.: US 11,571,567 B2
(45) Date of Patent: Feb. 7, 2023

(54) IONTOPHORESIS DEVICE FOR DRUG DELIVERY AND METHOD FOR MANUFACTURING THE SAME

(71) Applicant: BIOSENSOR LABORATORIES INC., Seoul (KR)

(72) Inventors: Myoung Hoon Jang, Seoul (KR); Joon Lee, Seoul (KR); Joo Hyun Song, Seoul (KR); Sung Koo Kang, Seoul (KR); Minwoong Jung, Incheon (KR); Jihyun Lee, Seoul (KR)

(73) Assignee: BIOSENSOR LABORATORIES INC., Seoul (KR)

( * ) Notice: Subject to any disclaimer, the term of this patent is extended or adjusted under 35 U.S.C. 154(b) by 1165 days.

(21) Appl. No.: 15/777,490

(22) PCT Filed: Jan. 5, 2016

(86) PCT No.: PCT/KR2016/000033
§ 371 (c)(1),
(2) Date: May 18, 2018

(87) PCT Pub. No.: WO2017/119519
PCT Pub. Date: Jul. 13, 2017

(65) Prior Publication Data
US 2018/0369579 A1 Dec. 27, 2018

(30) Foreign Application Priority Data
Jan. 5, 2016 (KR) .................. 10-2016-0000773

(51) Int. Cl.
*A61N 1/30* (2006.01)
*A61M 37/00* (2006.01)
*H01M 8/22* (2006.01)

(52) U.S. Cl.
CPC ............. *A61N 1/303* (2013.01); *A61M 37/00* (2013.01); *A61N 1/30* (2013.01); *H01M 8/227* (2013.01);
(Continued)

(58) Field of Classification Search
CPC .. A61N 1/0428; A61N 1/0432; A61N 1/0444; A61N 1/0448; A61N 1/325;
(Continued)

(56) References Cited

U.S. PATENT DOCUMENTS 4,744,787 A * 5/1988 Phipps ................. A61N 1/0448
604/20
5,071,537 A * 12/1991 Yamaguchi .......... G01N 27/301
204/414

(Continued)

FOREIGN PATENT DOCUMENTS

| CN | 102049195 A | 5/2011 |
| EP | 2 857 441 A1 | 4/2015 |

(Continued)

OTHER PUBLICATIONS

Extended European Search Report dated Jul. 3, 2019 in counterpart European Patent Application No. 16883905.8 (6 pages in English).

(Continued)

*Primary Examiner* — Nathan R Price
*Assistant Examiner* — Mark A Igel
(74) *Attorney, Agent, or Firm* — NSIP Law

(57) ABSTRACT

Provided are an iontophoresis device for drug delivery, a method for preparing the iontophoresis device, a kit including the iontophoresis device, and a method for delivering a drug by using the iontophoresis device.

20 Claims, 12 Drawing Sheets

(52) U.S. Cl.
CPC . *A61M 2037/0007* (2013.01); *A61M 2207/00* (2013.01); *H01M 2300/0002* (2013.01)

(58) Field of Classification Search
CPC ........ A61N 1/0496; A61N 1/30; A61N 1/303; A61K 9/0009; A61M 37/00
See application file for complete search history.

(56) References Cited

U.S. PATENT DOCUMENTS

| | | | | |
|---|---|---|---|---|
| 5,637,084 A * | 6/1997 | Kontturi | ............. | A61N 1/0448 604/20 |
| 5,647,844 A * | 7/1997 | Haak | ............. | A61N 1/0444 424/449 |
| 5,985,990 A * | 11/1999 | Kantner | ............. | A61L 15/58 424/448 |
| 6,119,036 A * | 9/2000 | Allen, Jr. | ............. | A61N 1/30 424/449 |
| 6,306,419 B1 * | 10/2001 | Vachon | ............. | A61K 9/7023 424/422 |
| 6,678,554 B1 * | 1/2004 | Sun | ............. | A61N 1/044 604/20 |
| 6,743,432 B1 | 6/2004 | Yanai et al. | | |
| 7,099,713 B2 * | 8/2006 | Browning | ............. | A61B 5/325 600/395 |
| 7,398,121 B2 * | 7/2008 | Matsumura | ............. | A61N 1/303 604/20 |
| 7,437,189 B2 * | 10/2008 | Matsumura | ............. | A61N 1/306 604/21 |
| 7,477,938 B2 * | 1/2009 | Sun | ............. | A61N 1/30 604/20 |
| 7,479,133 B2 * | 1/2009 | Sun | ............. | A61N 1/044 604/501 |
| 7,507,228 B2 * | 3/2009 | Sun | ............. | A61N 1/0428 604/20 |
| 7,574,256 B2 * | 8/2009 | Carter | ............. | A61N 1/0444 424/449 |
| 7,660,626 B2 * | 2/2010 | Tanioka | ............. | A61N 1/044 604/20 |
| 7,848,801 B2 * | 12/2010 | Carter | ............. | A61N 1/30 604/20 |
| 8,231,614 B2 * | 7/2012 | Dunning | ............. | A61N 1/0492 606/32 |
| 8,295,922 B2 * | 10/2012 | Kanamura | ............. | A61N 1/0448 604/20 |
| 8,332,028 B2 * | 12/2012 | Visco | ............. | A61N 1/0436 604/20 |
| 8,386,030 B2 * | 2/2013 | Kanamura | ............. | A61N 1/044 604/20 |
| 8,481,059 B2 * | 7/2013 | Cleary | ............. | A61L 15/44 424/400 |
| 8,706,261 B2 * | 4/2014 | Palti | ............. | A61N 1/326 607/154 |
| 8,834,454 B2 * | 9/2014 | Genosar | ............. | A61M 5/145 604/890.1 |
| 8,903,485 B2 * | 12/2014 | Imran | ............. | A61N 1/30 604/20 |
| 9,011,376 B2 * | 4/2015 | Genosar | ............. | A61M 5/14244 604/151 |
| 2002/0042587 A1 * | 4/2002 | Murdock | ............. | A61N 1/0448 604/20 |
| 2002/0062102 A1 * | 5/2002 | Keusch | ............. | A61P 9/04 604/20 |
| 2002/0072664 A1 * | 6/2002 | Katzenmaier | ............. | A61N 1/046 600/391 |
| 2004/0059282 A1 * | 3/2004 | Flock | ............. | A61N 1/303 604/20 |
| 2004/0138609 A1 * | 7/2004 | Fukuta | ............. | A61N 1/30 604/20 |
| 2004/0267231 A1 * | 12/2004 | Sun | ............. | A61N 1/30 604/20 |
| 2005/0019663 A1 * | 1/2005 | Nanno | ............. | H01M 50/109 429/235 |
| 2005/0169976 A1 * | 8/2005 | Mori | ............. | A61N 1/327 424/449 |
| 2006/0116628 A1 | 6/2006 | Matsumura et al. | | |
| 2009/0005824 A1 * | 1/2009 | Visco | ............. | A61N 1/0448 607/3 |
| 2009/0130189 A1 * | 5/2009 | Nicklasson | ............. | A61N 1/0432 424/449 |
| 2009/0254018 A1 | 10/2009 | Nakayama et al. | | |
| 2009/0299267 A1 * | 12/2009 | Durand | ............. | A61K 9/0009 604/20 |
| 2010/0189793 A1 * | 7/2010 | Meyer | ............. | A61N 1/044 424/484 |
| 2010/0204637 A1 * | 8/2010 | Imran | ............. | A61K 31/196 604/20 |
| 2012/0150266 A1 * | 6/2012 | Shalev | ............. | A61N 1/20 607/99 |
| 2013/0023850 A1 * | 1/2013 | Imran | ............. | A61K 9/0014 604/501 |
| 2014/0277273 A1 * | 9/2014 | Zhao | ............. | A61N 1/205 607/50 |

FOREIGN PATENT DOCUMENTS

| | | |
|---|---|---|
| JP | 7-504342 A | 5/1995 |
| JP | 9-56827 A | 3/1997 |
| JP | 2005-56827 A | 3/2005 |
| JP | 2011-200679 A | 10/2011 |
| KR | 10-2007-0078184 A | 7/2007 |
| KR | 10-0816554 B1 | 3/2008 |
| KR | 10-2011-0127371 A | 11/2011 |
| WO | WO 95/00200 A1 | 1/1995 |
| WO | WO 2009/144620 A1 | 12/2009 |

OTHER PUBLICATIONS

International Search Report dated Oct. 12, 2016, in corresponding International Application No. PCT/KR2016/000033.
Chinese Office Action dated Jun. 17, 2020 in counterpart Chinese Patent Application No. 201680077969.6 (18 pages in English).

* cited by examiner

IONTOPHORESIS DEVICE FOR DRUG DELIVERY AND METHOD FOR MANUFACTURING THE SAME

CROSS REFERENCE TO RELATED APPLICATION(S)

This application is a U.S. National Stage Application of International Application No. PCT/KR2016/000033, filed on Jan. 5, 2016, which claims the benefit under 35 USC 119(a) and 365(b) of Korean Patent Application No. 10-2016-0000773, filed on Jan. 5, 2016, in the Korean Intellectual Property Office.

TECHNICAL FIELD

One or more embodiments relate to an iontophoresis device for drug delivery and a method of preparing the device.

BACKGROUND ART

Methods for delivering a drug for the purpose of skin care or treatment may be oral administration, topical administration, intravenous administration, intramuscular injection, intradermal injection, and subcutaneous injection. Except the topical administration delivering a drug to a specific site of the body, these drug delivery methods generally deliver a drug to the whole body. These drug delivery methods are not appropriate for topically delivering a drug to a specific body tissue.

Therefore, methods such as natural orfice transluminal endoscopic surgery (NOTES) and iontophoresis for drug delivery to a specific body tissue have been developed. The iontophoresis is a drug delivery method that facilitates charged molecules to penetrate a tissue. FIG. 1 is a view that schematically illustrates a conventional iontophoresis device. Referring to FIG. 1, an iontophoresis device is a technique that penetrates an ion material into skin by using a direct current, where an ion material having positive characteristics is applied to a '+' electrode, and an ion material having negative characteristics to a '−' electrode to use a repulsive force that acts between ions having the same porality, and thus the ion materials may be easily penetrated into skin. Unlike a traditional transdermal administration by which a drug is passively absorbed, active deliver of a drug may be performed in an electric field when the iontophoresis device is used.

However, in the conventional iontophoresis device, an oxidation reaction occurs at a surface of an electrode attached on skin which may thus generate itching, pain, burning, and erythema on skin of the user using the iontophoresis device. Accordingly, an iontophoresis device including an electrode to prevent itching, pain, burning, and erythema phenomenons that may be generated during a process of delivering a drug to skin.

DETAILED DESCRIPTION OF THE INVENTION

Technical Problem

According to an embodiment, provided are an iontophoresis device for drug deliver, a method of delivering a material to an object by using the device, and a method of preparing the device, wherein the iontophoresis device that improves drug delivery through skin by using a reverse electrodialysis battery unit and is capable of arbitrarily controlling a current value without being limited by stacking layers since several tens to hundreds of layers may be stacked laterally instead of vertically stacking the layers for generating a current in the reverse electrodialysis battery unit. Technical problems aimed to be resolved by the embodiment of are not limited to technical problems described herein, and other technical problems may be inferred from other embodiments hereinafter.

Technical Solution

According to an embodiment, an iontophoresis device includes a reversed electrodialysis (RED) battery unit; intermediate units that are each connected to one of two surfaces of the battery unit and face each other; and one or two first or second material-containing units that are connected to a surface of one of the two intermediate units or a surface of each of the two intermediate units, wherein the intermediate units are configured such that a current generated from the battery unit flows the material-containing unit, and the material-containing unit is configured such that a material in the material-containing unit is delivered to an object by using the current generated from the battery unit.

According to another embodiment, provided is a method of delivering a material to an object by using the iontophoresis device.

According to another embodiment, provided is a method of preparing the iontophoresis device.

Advantageous Effects of the Invention

When an iontophoresis device according to an embodiment and a method of delivering a material to an object by using the iontophoresis device are used, drug delivery through skin may improve, and itching, pain, burning, and erythema phenomenons that may occur during a process of delivering drug into skin may be prevented by using the iontophoresis device including an electrode.

When a method of preparing the iontophoresis device according to another embodiment is used, a pluratliy of reversed electrodialysis battery units may be prepared in a large amount by using a dicing process.

BEST MODE

The terms used in this specification are those general terms currently widely used in the art in consideration of functions in regard to the inventive concept, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

As used herein, the terms "comprise" or "include" should not be understood as necessarily include all of various elements or several steps described in the specification, but the term should be understood as not including some of the elements or some of the steps, or further including additional elements or steps.

Also, the terms such as "first", "second", etc. including an ordinal number may be used herein to describe various components, but the components should not be limited by the terms. These terms are only used to distinguish one component from another.

The description of embodiments below should not be understood as limiting the scope of the inventive concept, and anything that would have been easily inferred by those of ordinary skill in the art needs to be understood as that belongs to the scope of these embodiments. Hereinafter, embodiments for illustration only will be described by referring to the attached drawings.

According to an embodiment, provided is an iontophoresis device.

Figure 1:
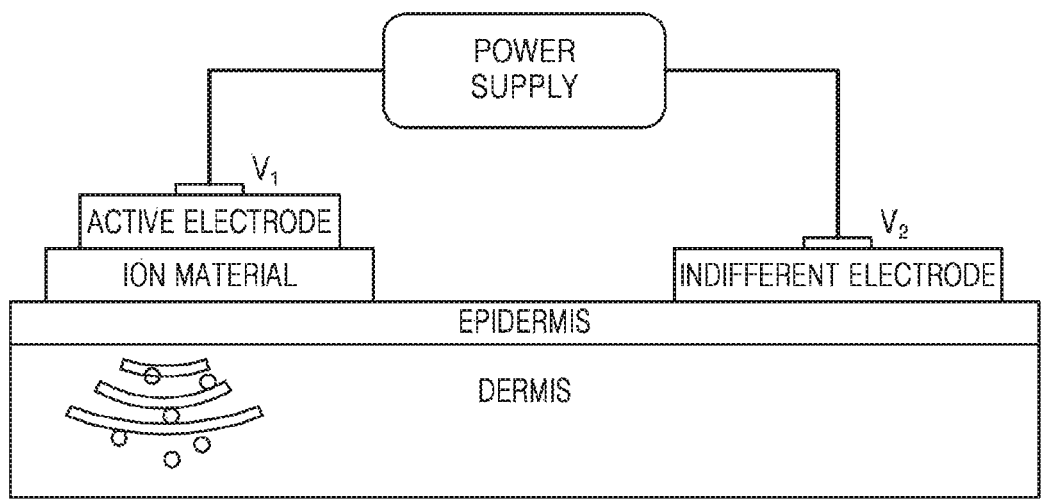
FIG. 1 is a schematic view of a conventional iontophoresis device.
Figure 2:
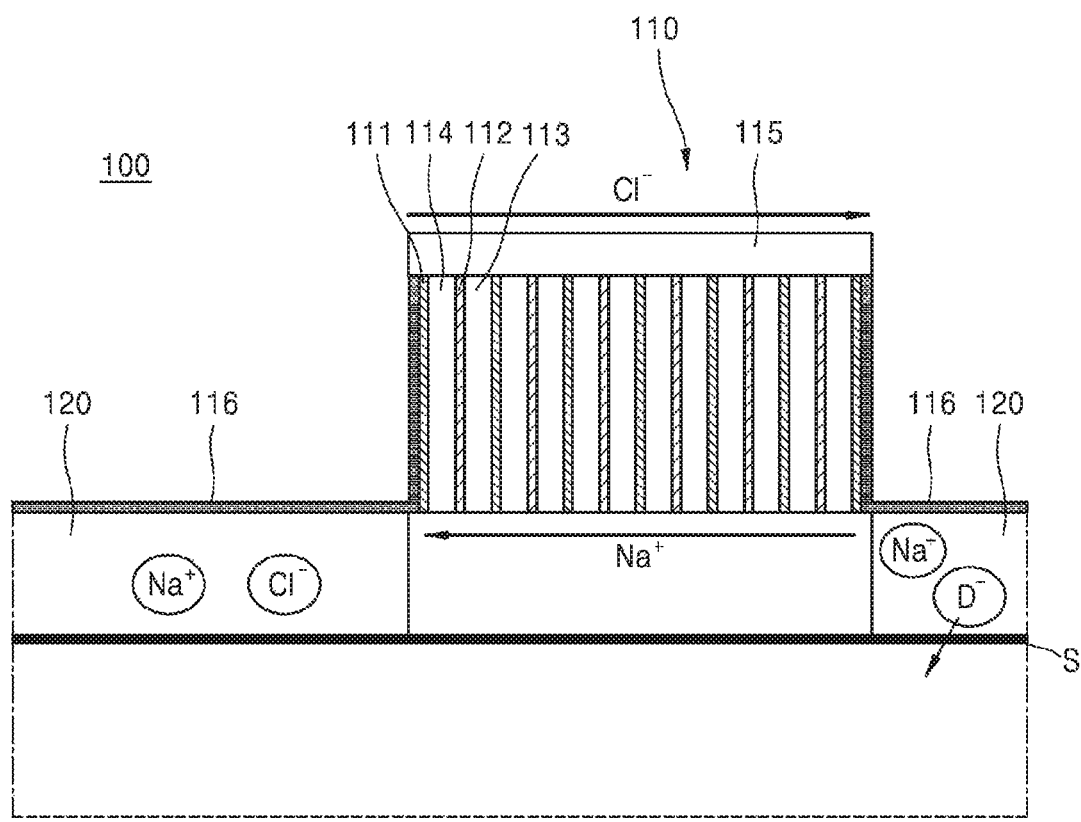
FIG. 2 is a schematic side view of an iontophoresis device according to an embodiment.
Figure 3:
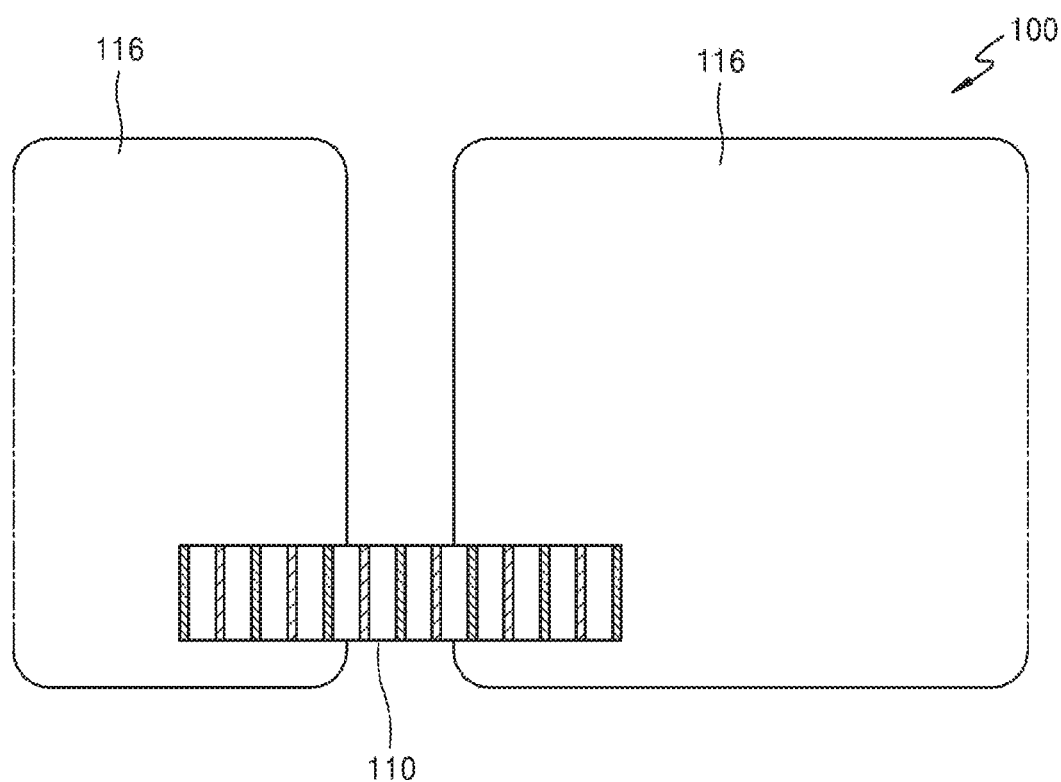
FIG. 3 is a schematic top view of the iontophoresis device according to an embodiment.

FIG. 2 is a schematic side view of an iontophoresis device 100 according to an embodiment. FIG. 3 is a schematic top view of the iontophoresis device 100 according to an embodiment. Referring to FIGS. 2 and 3, the iontophoresis device 100 includes a reversed electrodialysis (RED) battery unit 110; an intermediate unit 116 that is connected to each of two surfaces of the battery unit 110 facing each other; and one or two first or second material containing units 120 that are connected to one surface of one of the two intermediate units 116 or one surface of each of the two intermediate units 116, wherein the intermediate unit 116 is configured such that a current generated from the battery unit 110 flows through the material containing unit 120, and the material containing unit 120 is configured to deliver a material in the material containing unit 120 to an object by using the current generated from the battery unit 110.

The RED battery unit 110 may include a cation exchange membrane 111; an anion exchange membrane 112 that is disposed apart from the cation exachange membrane 111; and chambers 113 and 114 that are each at least partially defined with respect to the cation exchange membrane 111 and the anion exchange membrane 112 or disposed between the cation exchange membrane 111 and the anion exchange membrane 112, wherein the chambers 113 and 114 contain an electrolyte, the cation exchange membrane 111 and the anion exchange membrane 112 are alternately arranged so as to form a plurality of the cation exchange membranes 111 and a plurality of the anion exchange membranes 112 alternately arranged with each other, and the chambers 113 and 114 include a plurality of chambers 113 containing the electrolyte at a high concentration and a plurality of chambers 114 containing the electrolyte at a low concentration that are alternately arranged with each other.

In one embodiment, the iontophoresis device 100 may include a pluratliy of the cation exchange membranes 111, a plurality of the anion exchange membranes 112, and a pluratliy of the chambers 113 and 114 that contain an electrolyte, where each of the chambers 113 and 114 containing an electrolyte forms one layer, and the iontophoresis device 100 has 2 to 70 layers, 5 to 60 layers, 7 to 40 layers, 10 to 35 layers, or 15 to 30 layers.

The intermediate unit 116 may be connected to the cation exchange membrane 111 or the anion exchange membrane 112 that exists on an outer surface of the reversed electrodialysis battery unit 110. The intermediate unit 116 may include a conductive material, e.g., a carbon coating, or may be formed of conductive cloth or conductive fabric. The conductive cloth or conductive fabric may have a first layer that includes a synthetic resin and is formed on a surface connected to the material containing unit 120; a second layer that includes a conductive material and a synthetic resin and is formed on the first layer; a third layer that includes a conductive material and is formed on the second layer; a fourth layer that includes a conductive material and a synthetic resin and is formed on the third layer; and a fifth layer that includes a synthetic resin and is formed on the fourth layer. The conductive material may include silver, copper, aluminum, gold, carbon, or a combination thereof. The synthetic resin may include an acryl resin, a urethane resin, a silicon resin, a styrene resin, an aniline resin, an amino resin, an aminoalkyd resin, a vinyl acetate resin, an alkyd resin, an epoxy resin, a toluene resin, or a combination thereof. The intermediate unit 116 may allow a current generated from the battery unit 110 to flow through the material containing unit 120.

Also, the iontophoresis device 100 may further include a containiner 115 for accommodating the RED battery unit 110 and the material containing unit 120. The container 115 may accommodate the iontophoresis device 100 and may be disposed to expose at least a part of one surface of the material containing unit 120 that contacts an object.

Since the one surface of the material containing unit 120 may contact an objext S, to which a material is to be administered, a current generated from the reversed electrodialysis battery unit 110 may flow through the material containing unit 120 via the intermediate unit 116, and thus the material in the material containing unit 120 may be delivered to the object S. For example, cations (Nat) in the chamber 113 containing an electrolyte at a high concentration may penetrate through the cation exchange membrane 111 and migrate to the chamber 114 containing an electrolyte at a low concentration, and anions (Cl⁻) in the chamber 114 containing an electrolyte at a low concentration may penetrate through the anion exchange membrane 112 and migrate to the chamber 114 containing an electrolyte at a low concentration. Migration of the ions occurs at all of the cation exchange membranes 111, the anion exchange membranes 112, and the chambers 113 and 114, and thus an ion current is generated in the reverse electrodialysis battery unit 110, and thus outputs a current. That is, the anions (Cl⁻) may be emitted to the anion exchange membrane 112 that is disposed on the outer surface of the battery unit 110. Then, the anions (Cl⁻) migrate to the material containing unit 120 through the anion exchange membrane 112 disposed on the outer surface of the battery unit 110 and the intermediate unit 116, and thus a repulsive force may act on an anionic material $D^-$ included in the material containing unit 120. Similarly, the cations (Nat) migrate to the material containing unit 120 through the cation exchange membrane 111 disposed at the end of the battery unit 110 and the intermediate unit 116, and thus a repulsive force may act on a cationic material $D^+$ included in the material containing unit 120. Thus, for example, when a current is supplied to the material containing unit 120 through the cation exchange membrane 111 disposed on the outer surface of the battery unit 110 and the intermediate unit 116, the material $D^+$ may penetrate (be delivered) to an object through skin, and when a current is supplied to the material containing unit 120 through the anion exchange membrane 112 disposed on the outer surface of the battery unit 110 and the intermediate unit 116, the material $D^-$ may penetrate (be delivered) to an object through skin.

Figure 4:
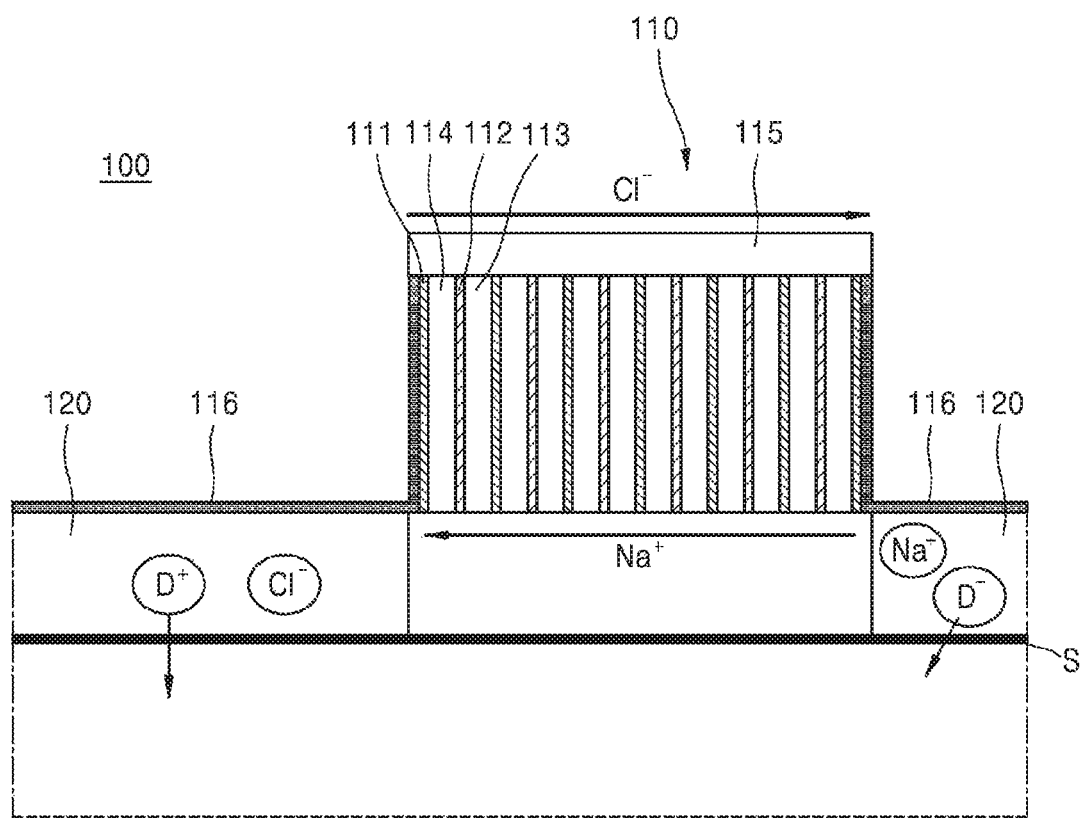
FIG. 4 is a schematic side view of the iontophoresis device according to an embodiment.

Referring to FIG. 4, the material to be delivered to an object may be included in both first and second material containing units 120. For example, the first or second material containing unit 120 may have the material to be delivered to an object in both the first and second material containing units 120 or may have the material to be delivered to an object only in the first material containing unit 120. When the material to be delivered to an object is included in both the first and second material containing units 120, the anions (Cl⁻) may be emitted through the anion exchange membrane 112 disposed on the outer surface of the battery unit 110. Then, a current may be supplied to the material containing unit 120 connected to the anion exchange membrane 112 disposed on the outer surface of the battery unit 110 through the intermediate unit 116, and thus the material $D^+$ may be delivered to the object S. The first or second material containing units 120 may not contact each other due to an insulator (not shown) or by physical separated configuration.

Also, a voltage or a current generated from the reversed electrodialysis battery unit 110 may be controlled by controlling types or thicknesses of the cation exchange membrane 111 and the anion exchange membrane 112 or volumes of the chambers 113 and 114. Regarding thicknesses that determine volumes of the chambers 113 and 114 containing an electrolyte, thicknesses of the chambers 113 and 114 disposed in a middle part of the battery unit 110 may be thicker that thicknesses of the chambers 113 and 114 disposed on the outside of the battery unit 110. In this regard, a voltage or a current output from the battery unit 110 may increase. Also, for example, a range of the voltage output from the battery unit 110 may be at least about 0.5 volts or higher, for example, about 0.5 volts to about 15 volts, about 1.0 volts to about 10 volts, about 1.5 volts to about 8.0 volts, about 2.0 volts to about 6.0 volts, about 2.0 volts to about 4.0 volts, or about 2.0 volts to about 3 volts. A range of the current output from the battery unit 110 may be at least about 0.1 mA or higher, for example, about 0.1 mA to about 10 mA, about 0.2 mA to about 8 mA, about 0.4 mA to about 6 mA, about 0.5 mA to about 4 mA, about 0.5 mA to about 2 mA, or about 0.5 mA to about 1 mA. The current may vary depending on a skin resistance, and the skin resistance may be in a range of about 1000 Ohm to about 3000 Ohm.

In one embodiment, the iontophoresis device 100 may be prepared in the form of a patch or a patch type for delivering a material through skin. One surface of the material containing unit 120 of the patch may be attached to the RED battery unit 110 through the intermediate unit 116, and the other surface may be attached to a protection layer (not shown), where the protection layer may include an adhesive material. Thus, when the protection layer is removed, the patch may be attached on skin. Also, the patch may be in any shape, for example, a rectangle, a circle, an oval, or a hexagon.

As used herein, the term "reverse electrodialysis (RED)" may denote a salinity gradient energy that is generated by a difference in salt concentrations of two solutions and, in one embodiment, may refer to a phenomenon of allowing a current to flow through the iontophoresis device 100. Therefore, the RED battery unit 110 may denote a device generating a current by using reverse electrodialysis. For example, as used herein, the RED battery unit 110 may generate a current by an ion concentration difference between electrolytes in a high-concentration electrolyte solution and a low-concentration electrolyte solution.

Also, since the iontophoresis device 100 according to an embodiment uses reverse electrodialysis, the iontophoresis device 100 may not require or have a separate power or an electrode. For example, the battery unit 110 may be the only current source for delivering a material to an object. The iontophoresis device 100 may be a current source for delivering a material to an object and may be formed of the battery unit 110 only, and the battery unit 110 may not have a separate power or an electrode. In order to generate a current by using the RED battery unit 110, the battery unit 110 may use an electrolyte solution. As used herein, the term "electrolyte" may refer to a material that is dissociated into ions in a solvent such as water to allow a current to flow, and the electrolyte solution may denote a solution such as water in which an electrolyte is dissolved. Thus, the electrolyte may be included in the electrolyte solution. The RED battery unit 110 generates a current by using a difference between a high-concentration electrolyte solution and a low-concentration electrolyte solution, where an amount of an electrolyte in the chamber 113 containing the electrolyte at a high concentration may be greater than an amount of an electrolyte in the chamber 114 containing the electrolyte at a low concentration. The chamber 114 containing the electrolyte at a low concentration may include a chamber that does not contain an electrolyte. For example, the electrolyte may be included in an electrolyte solution, and the chamber 113 containing the electrolyte at a high concentration may include the electrolyte solution of an ion concentration in a range of about 0.1 to about 20 mol/L, about 0.5 to about 15 mol/L, about 0.7 to about 10 mol/L, about 1.0 to about 8.0 mol/L, about 1.0 to about 2.0 mol/L, or about 1.2 to about 1.8 mol/L, and the chamber 114 containing the electrolyte at a low concentration may not include the electrolyte or may include the electrolyte solution of an ion concentration in a range of about 0.005 to about 10 mol/L, about 0.005 to about 8 mol/L, about 0.01 to about 6 mol/L, about 0.05 to about 6.0 mol/L, about 0.1 to about 4.0 mol/L, or about 0.1 to about 2.0 mol/L. The ion concentration of the electrolyte solution in the chamber 113 containing the electrolyte at a high concentration may be higher than the ion concentration of the electrolyte solution in the chamber 114 containing the electrolyte at a low concentration.

In another embodiment, the chambers 113 and 114 including the electrolyte may include electrolyte paste. The electrolyte paste may include a water-soluble polymer binder and an electrolyte. The water-soluble polymer binder may be, for example, at least one selected from the group consisting of a cellulose-based resin, xanthan gum, polyvinyl pyrrolidone, polyvinyl alcohol, a water-soluble (meth) acryl resin, polyether-polyol, and polyether-urea-polyurethane. When the electrolyte paste is prepared by mixing the water-soluble polymer binder and the electrolyte, a chamber including the electrolyte paste may be prepared. When the electrolyte paste is used as an electrolyte included in the chamber, a resistance may decrease, which may facilitate migration of the electrolyte in the chamber.

In another embodiment, the chambers 113 and 114 including the electrolyte may contain a hydrogel including an electrolyte. For example, the chamber 113 containing the electrolyte at a high concentration may contain a solid material including the electrolyte at a high concentration or a hydrogel including the electrolyte at a high concentration, or the chamber 114 containing the electrolyte at a low concentration may be empty or may contain a solid material including the electrolyte at a low concentration or a hydrogel including the electrolyte at a low concentration. When the solid material or the hydrogel is included, for example, when a salt (NaCl) in a solid state is included, the solid material or the hydrogel is dissolved in water as the water flows into the chamber and forms an aqueous electrolyte solution, which may generate a flow of ions. The solid material or the hydrogel may be any material that has water-solubility or permeability of an ionic material and has appropriate mechanical characteristics. Examples of the solid material or the hydrogel may include agar, polyethylene glycoldiacrylate (PEGDA), poly(2-hydroxyethyl methacrylate) (PHEMA), and an alginic acid such as sodium alginate, calcium alginate, or potassium alginate. Also, the solid material or the hydrogel may include a solid powder preparation of an ionic binding material.

The chambers 113 and 114 containing an electrolyte may have a woven form, and may be capable of absorbing an aqueous solution. For example, the woven form may be non-woven fabric. When the chambers 113 and 114 containing an electrolyte have a woven form and are capable of absorbing an aqueous solution, the electrolyte may be included in the chambers in the form of a powder. When the electrolyte exists in the form of a powder in the chambers of a woven form, a solution, for example the electrolyte, is dissolved in water as the water flows into the chambers, thus forming an aqueous electrolyte solution such that a flow of ions may occur. Also, the chambers 113 and 114 may be woven material impregnated with an electrolyte. The woven material impregnated with an electrolyte may be prepared by, for example, adding a woven material into a NaCl solution and performing a hot-air rolling process thereon. For example, the chamber 113 containing the electrolyte at a high concentration may be prepared by adding a woven woven material capable of absorbing an aqueous solution to a high-concentration NaCl solution and performing a hot-air rolling process thereon, and the chamber 114 including the electrolyte at a low concentration may be prepared by adding a woven material capable of absorbing an aqueous solution to a low-concentration NaCl solution and performing a hot-air rolling process thereon. Also, the chamber 114 containing the electrolyte at a low concentration may be formed of a woven material that is capable of absorbing an aqueous solution but is not impregnated with NaCl.

During activation, amounts of the electrolytes or ion concentrations of the electrolyte solutions in the chamber 113 containing the electrolyte at a high concentration and the chamber 114 containing the electrolyte at a low concentration may be different from each other, such that a voltage of at least about 0.5 volts or higher, or, for example, in a range of about 0.1 to about 15 volts, about 0.2 to about 10 volts, about 1.0 to about 8.0 volts, about 2.0 to about 6.0 volts, about 2.0 to about 4.0 volts, or about 2.0 to about 3 volts may be output. Also, amounts of the electrolytes or ion concentrations of the electrolyte solutions in the chamber 113 containing the electrolyte at a high concentration and the chamber 114 containing the electrolyte at a low concentration may be different from each other, such that a current of about 0.1 mA or higher, or, for example, in a range of about 0.1 to about 10 mA, about 0.2 to about 8 mA, about 0.4 to about 6 mA, about 0.5 to about 4 mA, about 0.5 to about 2 mA, or about 0.5 to about 1 mA, may be generated. Examples of the electrolyte may include NaCl, $MgCl_2$, AgCl, $CuCl_2$, $CaCl_2$), or a combination thereof.

As used herein, the term "ion-exchange membrane" may denote a membrane having a strong tendency to allow permeation therethrough of either cations or anions. The ion-exchange membrane may be a synthetic resin, and, for example, the synthetic resin may be cross-linked. Since the cation exchange membrane 111 has a negative charge, ions having a negative charge do not permeate therethrough as they are repelled by the cation exchange membrane 111, and only ions having a positive charge may permeate therethrough. For example, the cation exchange membrane 111 may be a cation exchange membrane having a sulfon group. On the other hand, the anion exchange membrane 112 has a positive charge, and thus ions having a positive charge do no permeate therethrough as they are repelled by the anion exchange membrane 112, and only ions having a negative charge may permeate therethrough. For example, the anion exchange membrane 112 may be an anion exchange membrane including tetravalent ammonium. Types of a monomer that forms the cation exchange membrane 111 may include 2-(meth)acrylamide-2-methylpropanesulfonic acid, 3-sulfopropane(meth)acrylate, 10-sulfodecane(meth)acrylate, and salts thereof; a carboxylic acid-type monomer, for example, 2-(meth)acryloylethylphthalic acid, 2-(meth)acryloylethylsuccinic acid, 2-(meth)acryloylethylmaleic acid, 2-(meth) acryloylethyl-2-hydroxyethylphthalic acid, 11-(meth)acryloyloxydecyl-1,1-dicarboxylic acid, and salts thereof; and a sulfuric acid-type monomer, for example, 2-(meth)acryloyloxyethyl dihydrogenphosphate, 2-(meth)acryloyloxyethyl phenyl hydrogen phosphate, 10-(meth)acryloyloxydecyl dihydrogenphosphate, 6-(meth)acryloyloxyhexyl dihydrogenphosphate, and salts thereof. Types of a monomer that forms the anion exchange membrane 112 may include N,N-dimethylaminoethyl(meth)acrylate, N,N-diethylaminoethyl(meth)acrylate, N,N-dimethylaminoethyl(meth)acrylate/methyl chloride, and N,N-diethylaminoethyl(meth) acrylate/methyl chloride. An ion exchange capacity (IEC) of the cation exchange membrane 111 or the anion exchange membrane 112 may be about 0.5 meg/g or higher or about 1.0 meg/g or higher, or, for example, in a range of about 0.5 to about 20.0 meg/g, about 1.0 to about 10.0 meg/g, about 2.0 to about 10.0 meg/g, or about 5.0 to about 10.0 meg/g. Also, permeation selectivity of the cation exchange membrane 111 or the anion exchange membrane 112 may be about 70% or about 80% or higher, or, for example, in a range of about 80 to about 100%, about 90 to about 100%, or about 95 to about 100%.

In one embodiment, the iontophoresis device 100 may further include a spacer (not shown) to separate the cation exchange membrane 111 and the anion exchange membrane 112. The spacer may be the same as the chambers 113 and 114 containing an electrolyte. The spacer may prevent the ion exchange membranes from being attached to each other and may include, for example, a net structure formed of polypropylene or polyethylene; sponge; tape; a woven material, for example, fabric; or a non-woven material. Also, the spacer may serve as a support that supports the cation exchange membrane 111, the anion exchange membrane 112, and the chambers 113 and 114 containing an electrolyte. The support may be, for example, a gasket.

The container 115 may maintain and support elements in the RED battery unit 110. For example, the container 115 may be configured such that a solution in the chambers 113 and 114 may not leak. Also, a portion of the container 115 may serve as a spacer (not shown), for example, by using double-sided tape, in addition to the spacer described above. Also, the container 115 may be an insulator, and a material of the container 115 may be any material conventionally used as an insulator. Examples of the material may include cellophane, cellulose acetate, ethylcellulose, plasticized vinyl acetate-vinyl chloride copolymers, polyethylene terephthalate, nylon, polyethylene, polypropylene, polyvinylidene chloride, paper, cloth, and aluminum foil.

Also, the material containing unit 120 may include a material having a charge or a polarity. The material containing unit 120 may include a solvent having ion conductivity which may be a solvent known in the art. The material containing unit 120 may be configured such that the material to be delivered to an object is included in hydrogel, cellulose, agarpse, gelatin, or collagen. Also, for example, the material containing unit 120 may include an aqueous solution or a buffer solution including or containing a material having a charge or a polarity; or a hydrogel or a matrix. The material included in the material containing unit 120 may be mixed with an enhancer that promotes delivery of the material. The enhancer may be roughly classified into an enzymatic enhancer and a non-enzymatic enhancer. Examples of the enzymatic enhancer may include enhancers using a proteolytic enzyme such as papain, trypsin, pepsin, and bromelain, and examples of the non-enzymatic enhancer may include enhancers using non-enzymatic materials such as lactam compounds, ethyl acetate, ethyl alcohol, dioxolane, nonionic surfactants, propyleneglycol, caprylic acid, capric triglyceride, and n-decylmethylsulfoxide. The enhancers may be appropriately mixed and used according to the material to be delivered. Also, the matrix material may include esters of acrylic acid or methacrylic acid and an acryl or methacryl resin such as a polymer of an alcohol. Examples of the alcohol may include butanol, pentanol, isopentanol, 2-methylbutanol, 3-methylpentanol, 2-ethylbutanol, isooctanol, decanol, or dodecanol. Also, examples of the polymer may include a copolymer with an ethylenically unsaturated monomer such as acrylic acid, methacrylic acid, acrylamide, methacrylamide, N-alkoxymethylacrylamide, N-alkoxymethylmethacrylamide, N-t-butyl acrylamide, itaconic acid, vinyl acetate, N-branched alkylmaleamate glycol diacrylate, or a mixture thereof, as well as a homopolymer. Other examples of the matrix material may include natural or synthetic rubber such as styrene-butadiene, butyl ether, neoprene, polyisobutylene, polybutadiene, and polyisoprene; cellulose derivatives such as polyvinyl acetate, urea formaldehyde resins, phenol formaldehyde resins, resorcinol formaldehyde resins, ethylcellulose, nitrocellulose, cellulose acetate butyrate, and carboxymethylcellulose; and natural gums such as guar, acacia, pectin, starch, dextrin, albumin, gelatin, and casein. As is well known in the art, the materials may include a binder and a stabilizing agent. Also, examples of the object to which the material is delivered by the material containing unit 120 may include humans and mammals for different purposes, and examples of the object may include humans, monkeys, mice, rats, rabbits, sheep, cows, dogs, horses, and pigs.

The material having a charge or a polarity included in the material containing unit 120 may have a charge due to the material itself having a charge in an ion-conductive medium in the material containing unit 120 or may have a charge or a polarity due to solvation. The material having a charge or a polarity may include a physiologically active material or drug. A molecular weight (MW) of the material may be, for example, in a range of about 100 to about 2000, about 200 to about 2000, about 300 to about 1000, about 300 to about 800, or about 400 to about 7000. Also, the material may include a whitening agent, an anti-wrinkle agent, a pharmaceutical agent, or a combination thereof. Examples of the whitening agent may include a *Broussonetia kazinoki* extract, niacinamide, adenosine, arbutin, ethyl ascorbyl ether, an oil-soluble licorice extract, ascorbyl glucoside, ascorbyl tetraisopalmitate, magnesium ascorbyl phosphate, alpha-bisabolol, or a combination thereof. Examples of the anti-wrinkle agent may include retinol, retinyl palmitate, adenosine, polyethoxylated retinamide, acetyl hexapeptide-3 or-8, acetyl octapeptide-3, acetyl tetrapeptide-5, palmitoyl pentapeptide, copper peptide, palmitoyl oligopeptide, palmitoyl dipeptide-10, palmitoyl tripeptide-1, palmitoyl tetrapeptide-7, palmitoyl pentapeptide-3, palmitoyl hexapeptide-12, pentapeptide-18 (Leuphasyl), or a combination thereof. Examples of the drug may include a composite preparation that is selected from the group consisting of alkaloids, NSAIDs, alpha2 adrenergic agonists, opioids, NMDA antagonists, GABA agonists, nonopioidic central anesthetics, and anti-inflammatory agents. In particular, the alkaloid may include caffeine or nicotine. The drug may include each of a NSAID and an alpha2 adrenergic agonist, a NSAID and an opioid, NSAID, an opioid and an alpha2 adrenergic agonist, a NMDA antagonist, or an alpha2 adrenergic agonist and a NSAID. Regarding viral diseases accompanied by pain and skin lesions such as herpes zoster or herpes, for example, an antiviral agent and an anesthetic (e.g., an opioid, a topical anesthetic, or a capsaicin) may be included in the drug. Regarding cancer pain or chronic pain, for example, an opioid and an opioid antagonist may be included in the drug. The NSAIDs may include acetaminophen, acyclofenac, celecoxib, choline magnesium trisalicylate, diclofenac sodium, etodolac, fenoprofen, ibuprofen, indomethacin, ketoprofen, ketorolac, tromethamine, Ronazolac calcium, meloxicam, naproxen, pyrocicam, rofecoxib, salsarate, sulindol, and tenosicam. The alpha2 adrenergic agonists may include clonidine, tizanidine, medetomidine, paradomidine, and brimonidine. The opioids may include morphine, codeine, fentanyl, alfentanil, sufentanil, remifentanil, hydromorphine, oxymorphine, hydrocodone, levorphanol, methadone, meperidine, buprenorphine, butorphanol, pentazocine, and nalbuphine. The NMDA antagonists may include ketamine and dextromethorphan. The GABA agonists may include diazepam, lorazepam, and baclofen. Steroids may include prednisolone, dexamethasone, triamcinolone, betamethasone, diflucortolone, monometasone, methylprednisolone, hydrocortisone, clobetasol, aclomethasone, clomethasone, and fluorocinolone. The nonopioidic central anesthetics may include tramadol, and anti-viral agents may include acyclovir, palmclover, and valacyclovir.

Local anesthetics may include tetracaine, lidocaine, mephibacaine, bupivacaine, lopivacaine, and levo-bupivacaine. Opioid antagonists may include naloxone and naltrexone. In addition, the material may be a protein, for example, a therapeutic protein. The protein may be a modified protein or an ionized or ionizable form of the protein so as to be contained and delivered in the material.

Figure 5A:
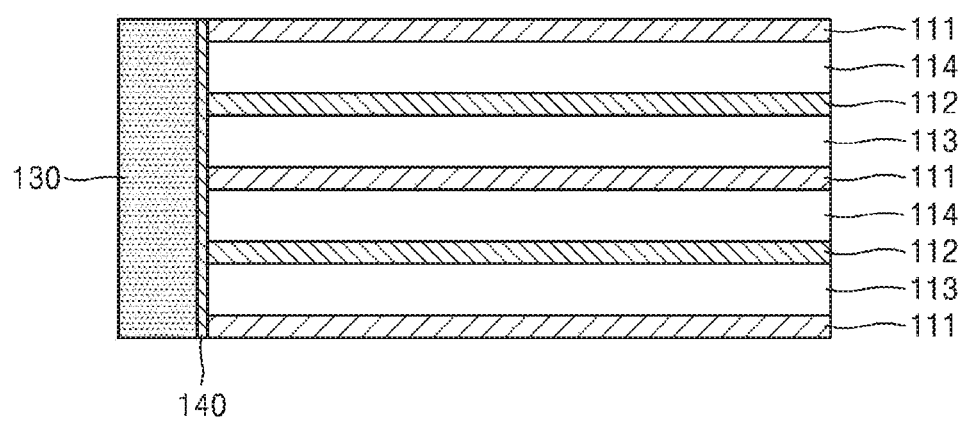
FIG. 5 is a schematic view that illustrates an activation principle of the iontophoresis device according to an embodiment.
Figure 5B:
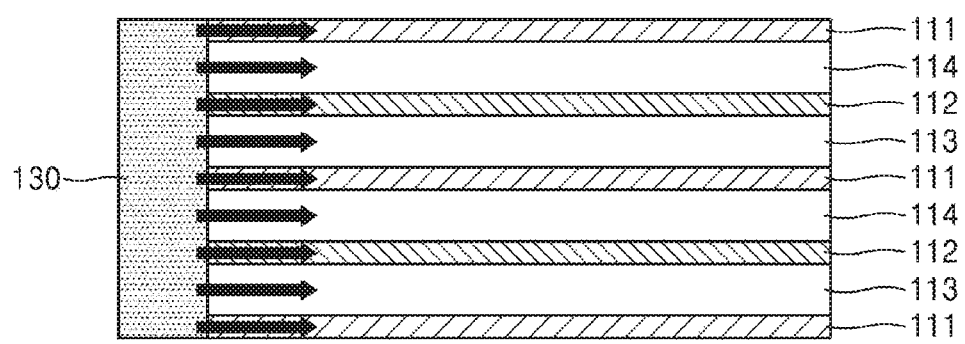
Figure 5C:
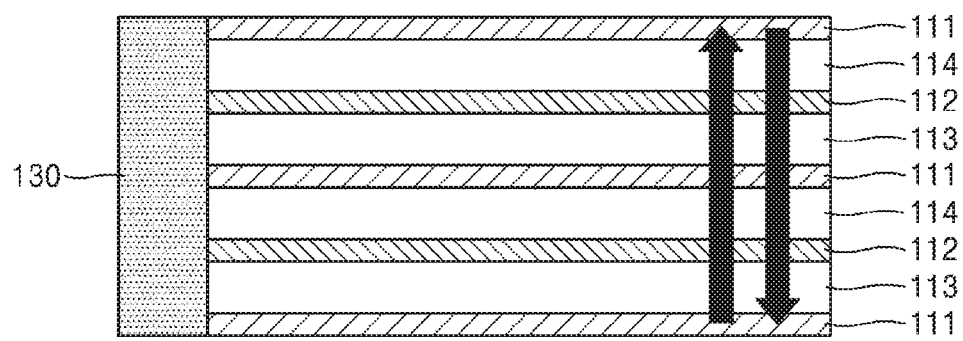

FIG. 5 illustrates an example of an iontophoresis device that is being activated. In the iontophoresis device according to an embodiment, as shown in FIG. 5A, a water-permeable membrane 140 may be disposed on at least a portion of a side-wall located between the cation exchange membrane 111 and the anion exchange membrane 112 as a side-wall of the chambers 113 and 114. Also, a water supply unit 130 that supplies water to the chambers 113 and 114 may be connected to at least one portion of the side-wall of the chambers 113 and 114. The water supply unit 130 and the chambers 113 and 114 may fluidically communicate via a flow path or a channel (not shown). A means or a valve for controlling the fluidic communication may be further included in the iontophoresis device. The side-wall used herein may denote a surface that is not a surface facing the chambers 113 and 114. Subsequently, as shown in FIG. 5B, water in the water supply unit 130 may flow into the chambers 113 and 114 through the water-permeable membrane 140, and, in this regard, as shown in FIG. 5C, the flow of ions described above may occur. In addition to the water-permeable membrane 140 or the water supply unit 130, a device may be activated by an arbitrary means so as to generate an electrolyte ion concentration difference in the chambers 113 and 114 of the device. For example, the device may be activated by supplying water to the device for activation before and after a user applies the device onto skin.

In another embodiment, the iontophoresis device 100 may include a control unit (not shown) to control a flow of ions. The control unit may be electrically connected with the RED battery unit 110. The control unit may include a switch device, a pH sensor, or a salt sensor. For example, the sensors may detect a flow of ions or an output of a current in the iontophoresis device 100 and may control the flow of ions or the output of a current by using the switch device. In the control unit, information about delivery characteristics of a material (a drug) in the material containing unit 120 to skin may be stored. For example, the control unit may include a microprocessor that stores data about iontophoresis characteristics of a particular material (drug) included in the iontophoresis device 100. The data may include a relationship between conditions of particular current and/or ion flow and a delivery rate when the particular material (drug) is delivered into a body through skin by using the iontophoresis device described above under the conditions. The microprocessor may include a control algorithm according to delivery characteristics of a material included in the material containing unit 120 to skin. Also, one who receives administration of the material or a doctor, may determine a basal administration level, i.e., an intensity of a basal current, of the material (drug) according to the data included in the microprocessor and may administer the material (drug). During administration of the material according to the basal administration level, when additional administration is need to the patient, for example, when the patient has a pain and the material (drug) being administered at the basal rate is a painkiller, additional material (drug) delivery may be provided in case the pain is not reduced by the basal administration. In this case, conditions of the material (drug) delivery may be determined base don the relationship between the material (drug) administration conditions stored in the microprocessor and the administration rate. The control unit may be configured to control an intensity of a current that is supplied to the skin of a user. The intensity of a current does not need to be automatically controlled, but the intensity of a current may be controlled according to the need of the patient or a practitioner. Also, the control unit may be configured such that a current being supplied to the skin of a user to be automatically on/off at a predetermined time interval. As described above, a feature of an electrical circuit that performs a current control function is obvious to those of ordinary skill in the art, and thus the detailed description regarding the feature will be omitted.

In another embodiment, the iontophoresis device 100 may include a display unit (not shown) that is electrically connected to the control unit. The display unit may display an amount and a rate of the material (drug) being administrered and a remaining amount of the material (drug) under particular conditions according to the data in the control unit. The display unit includes a display device known in the art. For example, the display device may be liquid crystal display (LCD), plasma display panel (PDP), Brown Tube, or light emitting diode (LED). In particular, the display unit is connected to the control unit, and the display unit may display at least one or more information selected from the group consisting of an amount of the the material (drug), an amount of the material (drug) remaining in a device, a delivery rate of the material (drug), and an amount of the material (drug) that needs to be delivered, while delivering the material (drug). The patient or practitioner (doctor) may determine whether to further additional administration of the material (drug) or to stop the administration based on an administration amount and an administration rate of the material (drug) disoplayed on the display unit.

According to another embodiment, provided is a kit including the iontophoresis device.

The kit may further include a drug. For example, the iontophoresis device may be provided together with a drug contained in a particular container as a kit, while a material to be delivered to an object is not included in the iontophoresis device. The drug may be provided as a composition including the drug or in the form of a drug powder. For example, the composition including the drug may be provided in the form of cream, gel, liquid, essence, or serum that includes the drug. The composition including the drug has a certain viscosity or higher, and thus when a user may apply the drug on a material-containing part to deliver the drug into the body. Also, the kit may further include an aqueous solution for activating the iontophoresis device. Those of ordinary skill in the art may appropriately select a preparation of the drug, the corresponding feature of a material containing unit, and components of the drug according to an aspect of the use. When the iontophoresis device, the drug, and/or the aqueous solution are provided as a kit, the user may apply the drug to the iontophoresis device and activate the iontophoresis device by using the aqueous solution to contact the drug to skin of the user or another person, and thus the drug may be delivered into the body.

Accoding to another embodiment, provided is a method of delivering a material to an object by using the iontophoresis device.

The method may include generating a current by forming a flow of ions between neighboring chambers by caion or anion exchange membranes by supplying water to the chambers; and delivering a material in a material containing unit by using the generated current.

In one embodiment, the method of delivering a material to an object may include generating a flow of ions between neighboring chambers among chambers including an electrolyte at a high concentration and chambers including an electrolyte at a low concentration; generating a current by the flow of ions; and delivering a material in a material containing unit to an object through an intermediate unit by using the generated current. The method may further include supplying an aqueous solution to the chambers to generate an ion concentration difference in electrolyte solutions in the chambers before the generating of a flow of ions between neighboring chambers. Thus, the method according to an embodiment may include generating a current by reversed electrodialysis; and delivering a material in a material containing unit to an object through an intermediate unit by using the generated current.

The iontophoresis device and features therein are the same as described above.

In one embodiment, the method may further include contacting the iontophoresis device to an object. The contacting step may be performed before or after the generating of an ion concentration difference of an electrolyte solution between the chambers or the generating a current by forming of a flow of ions between neighboring chambers.

The generating of a current may be, as described above, occurred by a flow of ions formed by an ion concentration difference in electrolyte solutions in at least two of the chambers, and, for example, may include generating a current by reversed electrodialysis as described above.

The method may not have supplying a power for delivering a material to an object. For example, the method may not have supplying a power for delivering a material to an object except a RED battery unit introduced to the iontophoresis device.

According to another embodiment, provided is a method of preparing the iontophoresis device.

Figure 6:
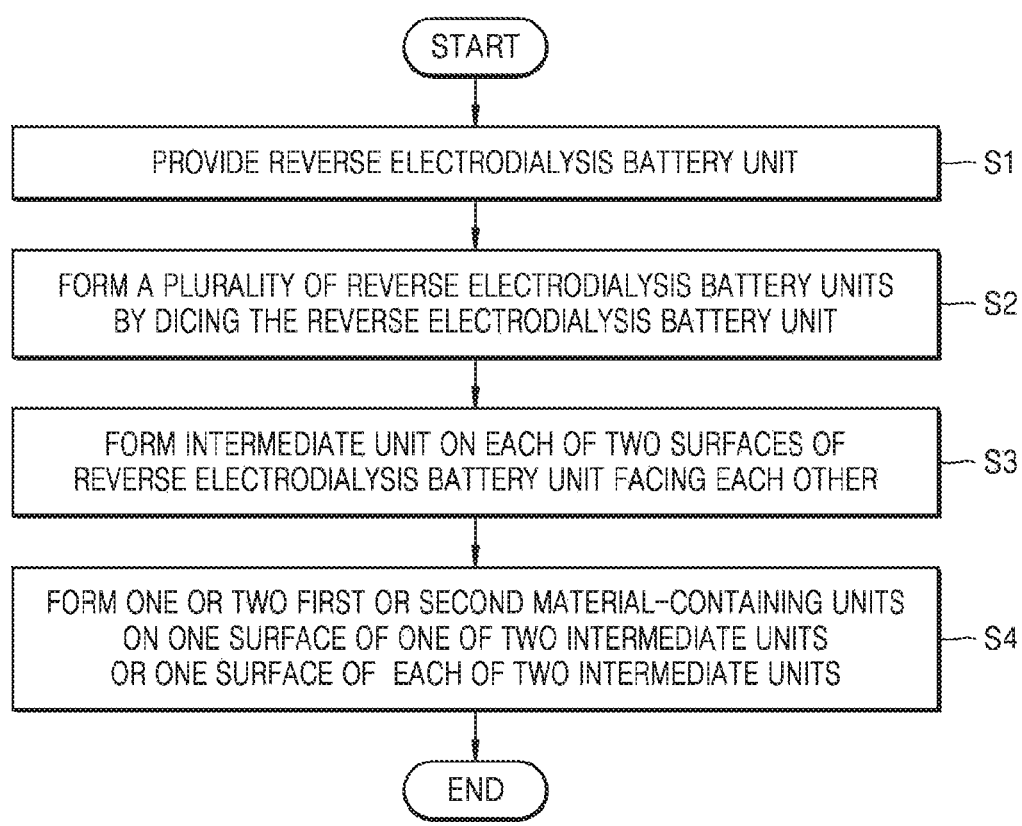
FIG. 6 is a schematic view that illustrates a method of preparing the iontophoresis device according to an embodiment.

Referring to FIG. 6, the method includes providing a RED battery unit (S1); forming two intermediate units on each of two surfaces of the RED battery unit facing each other (S3); and forming one or two first or second material containing units on one surface of one of the two intermediate units or one surface of each of the two intermediate units (S4), wherein the intermediate units are configured such that a current generated form the battery unit may flow through the material containing unit, and the material containing unit is configured to deliver a material in the material containing unit to an object by using the current generated from the battery unit.

Further referring to FIG. 6, in another embodiment, provided is a method of preparing a plurality of iontophoresis devices. The method may include providing a RED battery unit (S1); dicing the RED battery unit to form a plurality of RED battery units (S2); forming two intermediate units on each of two surfaces of each of the plurality of RED battery units, wherein the two surfaces of face each other (S3); and forming one or two first or second material containing units on one surface of one of the two intermediate units or one surface of each of the two intermediate units (S4), wherein the intermediate units are configured such that a current generated form the battery unit may flow through the material containing unit, and the material containing unit is configured to deliver a material in the material containing unit to an object by using the current generated from the battery unit The iontophoresis device and features therein are the same as described above.

Figure 7:
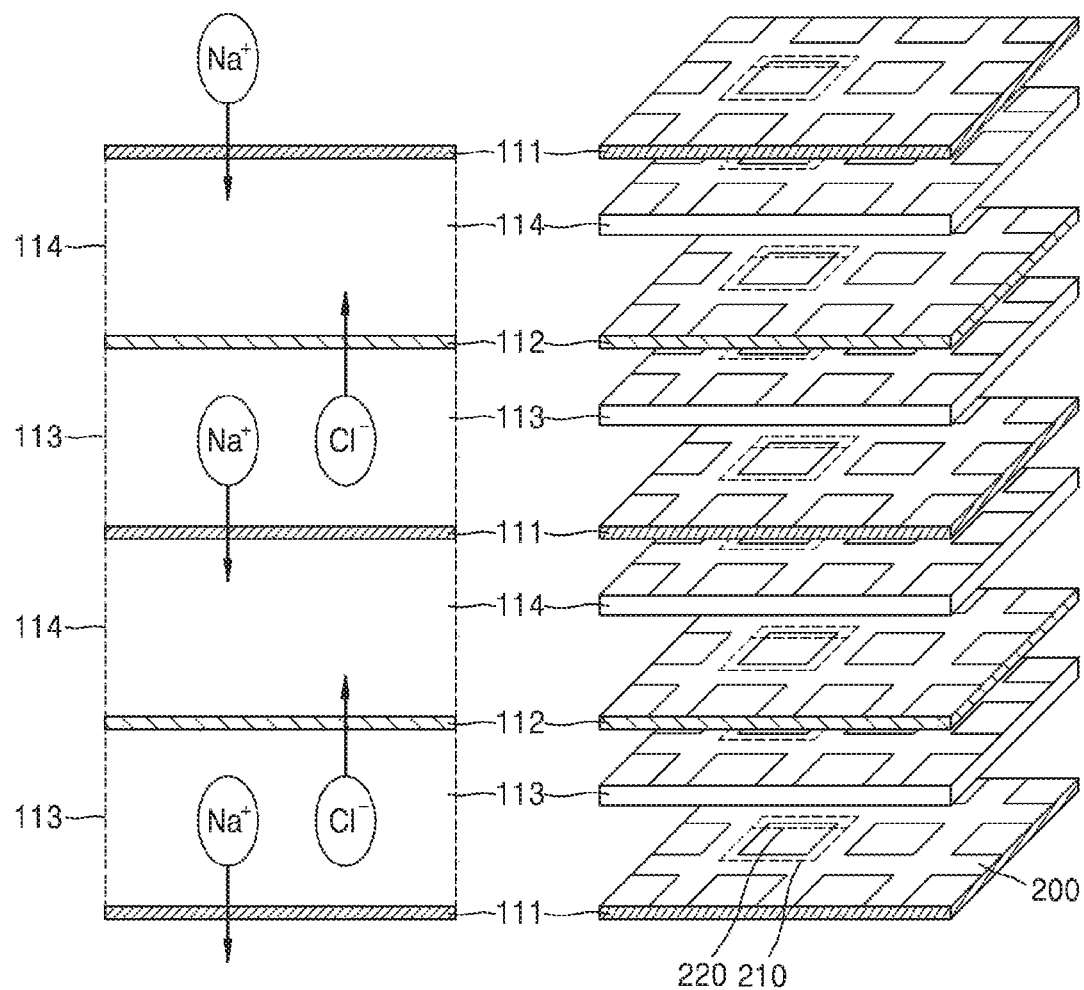
FIG. 7 is a schematic view that illustrates a method of prepareing a reversed electrodialysis battery unit of the iontophoresis device according to an embodiment.

Referring to FIG. 7, the providing of the RED battery unit may include forming a cation exchange membrane 111; forming an anion exchange membrane 112 that is disposed apart from the caion exchange membrane 111; and forming chambers 113 and 114 that are at least partially defined by the cation exchange membrane and the anion exchange membrane and contain an electrolyte between the cation exchange membrane 111 and the anion exchange membrane 112, wherein a plurality of the cation exchange membranes 111 and a plurality of the anion exchange membranes 112 are arranged alternating to each other, and the chambers 113 and 114 may include chambers 113 containing an electrolyte at a high concentration and chambers 114 containing an electrolyte at a low concentration that are arranged alternating to each other. Also, the providing of the RED battery unit may further include controlling a current or a voltage of the battery unit by changing a volume of the chambers 113 and 114 containing an electrolyte. Also, the providing of the RED battery unit may be forming a plurality of the cation exchange membranes 111, anion exchange membranes 112, and chambers 113 and 114 containing the electrolyte, where each of the chambers 113 and 114 containing an electrolyte constitues one layer, and the the RED battery unit has 2 to 70 layers. Also, the providing of the RED battery unit may include inserting an electrolyte to the chambers 113 and 114 containing an electrolyte. The inserting of the electrolyte is the same as described above.

Further referring to FIG. 7, the method may further include dicing the RED battery unit to form a plurality of RED battery units. For example, the providing of the RED battery unit may further include (200) applying a binder in a lattice shape in each step while forming the cation exchange membrane 111, the anion exchange membrane 112, and the chambers 113 and 114 containing an electrolyte. Thereafter, the method may further include (210) cutting the reversed electrodialysis battery unit along a part of the lattice shape; or the (210) cutting the reversed electrodialysis battery unit along a part of the lattice shape further including (220) cutting such that at least one surface of the reversed electrodialysis battery unit is exposed without the binder.

Also, in the dicing of the RED battery unit, the RED battery unit includes a cation exchange membrane; an anion exchange membrane that is disposed apart from the cation exchange membrane; and a chamber that is at least partially defined by the cation exchange membrane and the anion exchange membrane and contains an electrolyte, wherein a plurality of the cation exchange membranes and a plurality of the anion exchange membranes are disposed alternating to each other, and the chamber comprises a plurality of chambers comprising the electrolyte at a high concentration; and a plurality of chambers comprising the electrolyte at a low concentration that are disposed alternating to each other. The dicing of the RED battery unit may refer to cutting the RED battery unit into a small block or in the form of dice by using an appropriate blade.

Also, the method may further include inserting a material to be delivered to an object, for example, a material having a charge or a polarity, in the first or second material containing unit.

Figure 8:
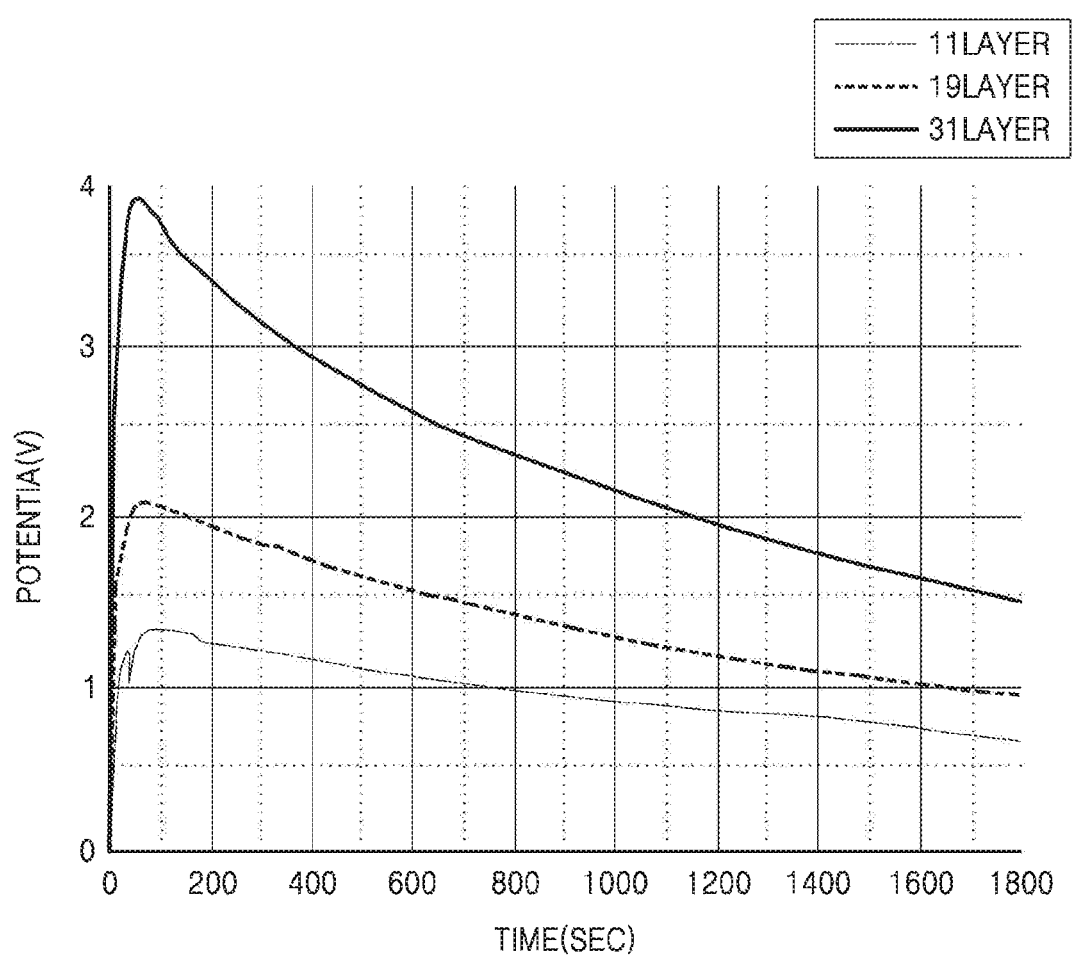
FIG. 8 is a graph that illustrates change in a voltage of the reversed electrodialysis battery unit of the iontophoresis device according to an embodiment in time.

FIG. 8 is a graph illustrating a change in voltage of the RED battery unit of the iontophoresis device in time, according to an embodiment. In order to confirm a change in voltage in time in FIG. 8, the RED battery unit was configured as follows. A non-woven fabric having a thickness in a range of about 0.2 to about 0.5 mm was used to form a chamber containing an electrolyte. A cation exchange membrane and an anion exchange memebrane were available from ASAHI GLASS Co. SBX tape (available from CROSS) was used as a spacer, a container, and a support for attaching the non-woven fabric, the cation exchange membrane, and the anion exchange membrane. Holes were formed in the SBX tape to allow ion exchange, and thus a space for locating a solution in the chamber containing an electrolyte was secured. Also, a predetermined amount of a NaCl powder was placed on the non-woven fabric so that a concentration of the chamber containing an electrolyte at a high concentration was 1.72 M and a concentration of the chamber containing an electrolyte at a low concentration was 0.011 M. Components of the RED battery unit were prepared as described above, and the components were stacked in the staking order of the RED battery unit described above. A size of the chamber was 1.5 cm×1.3 cm, and the RED battery units having 11 layers, 19 layers, and 31 layers were each prepared with the chamber as one layer, and voltage changes in time were measured. The measurement of voltages in time was performed for 40 minutes after supplying and activiating the prepared RED battery unit. Voltages and currents were measured by contacting a copper plate to the RED battery unit by using a current meter, digital multimeter 34410A, available from Keysight.

As shown in FIG. 8, it may be known that the RED battery unit has a tendency to form a particular voltage and to continue to decrease once reaching the peak voltage after being activated. However, despite the continuous decrease, it may be confirmed that the voltage was sufficient enough to deliver the material in the material containing unit to the object. Also, it may be confirmed that the output peak voltage increased as the number of the chambers containing an electrolyte increased, where the chamber containing an electrolyte constituted one layer.

Figure 9A:
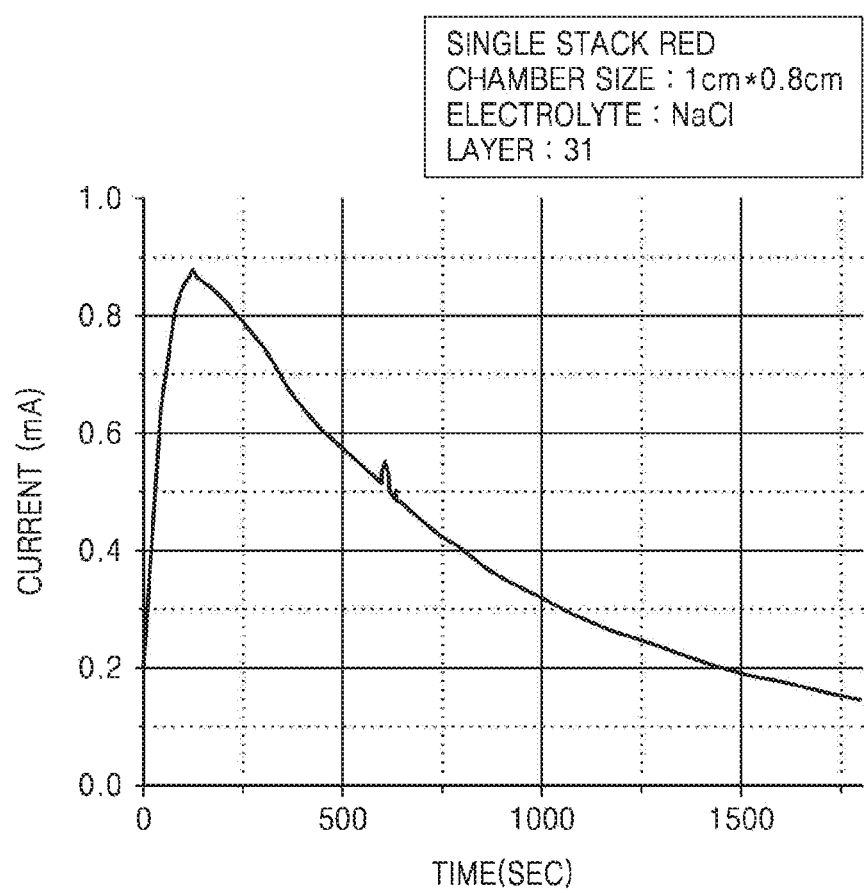
FIG. 9 is a graph that illustrates change in a current of the reversed electrodialysis battery unit of the iontophoresis device according to an embodiment in time.
Figure 9B:
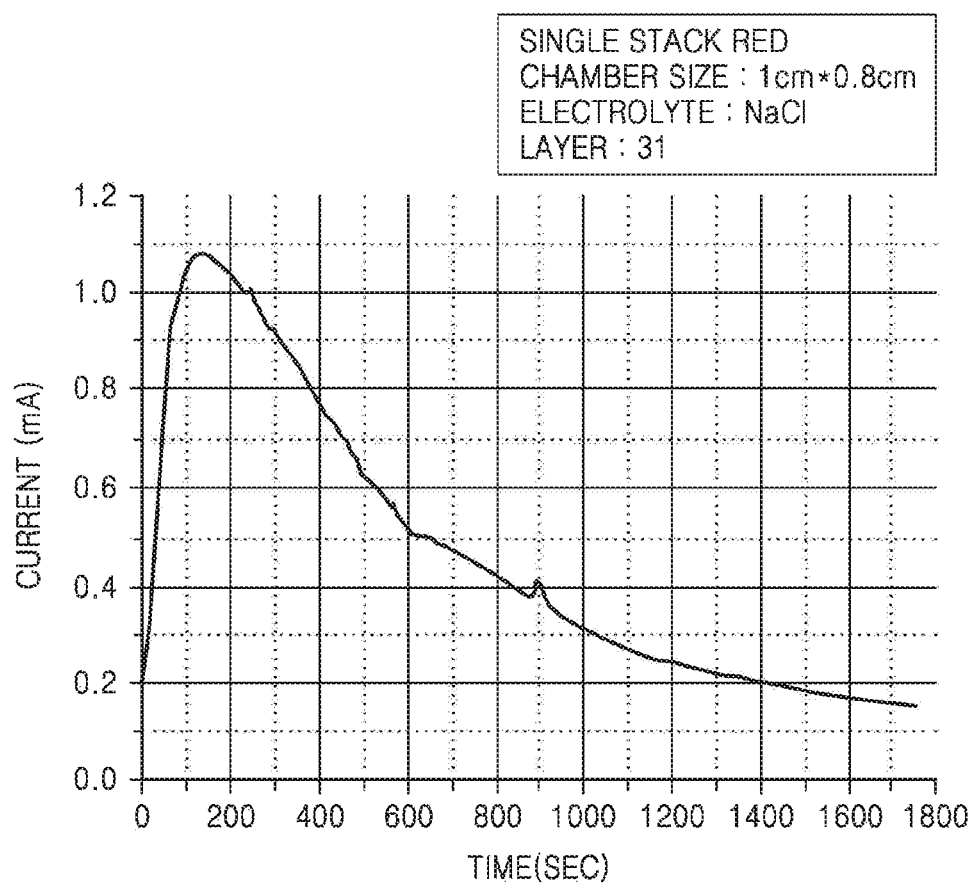

FIG. 9 is a graph illustrating a change in current of the RED battery unit of the iontophoresis device in time, according to an embodiment. In order to confirm a change in current in time in FIG. 9, the RED battery unit was prepared in the same manner as in preparation of the RED battery unit for the measurement of FIG. 6, except that the number of chamber layers was 31, a size of the chamber was 1 cm×0.8 cm, and concentrations of the chambers were changed. A concentration in the chamber containing an electrolyte at a high concentration was 1.72 M in FIG. 9A, and 5 M in FIG. 9B. A concentration in the chamber containing an electrolyte at a low concentration was 0.011 M.

As shown in FIG. 9, it may be known that the RED battery unit has a tendency to form a particular current and to continue to decrease once reaching the peak current after being activated. However, despite the continuous decrease, it may be confirmed that the current was sufficient enough to deliver the material in the material containing unit to the object. Also, it may be confirmed that a current of greater intensity was formed when a concentration difference of electrolytes increased or a concentration of the chamber containing an electrolyte increased.

Figure 10:
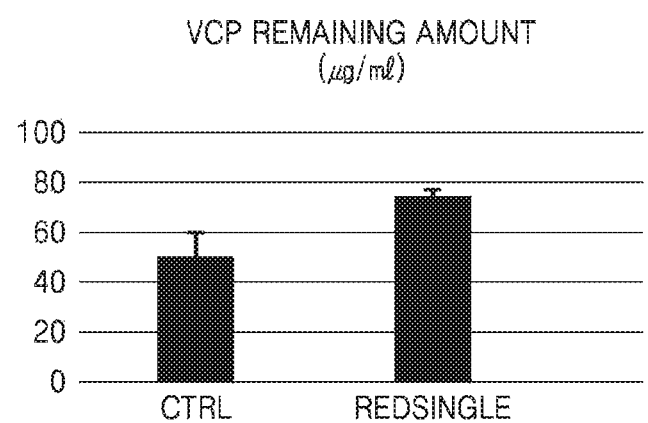
FIG. 10 is a graph that illustrates drug delivery effects of the iontophoresis device according to an embodiment in time.

FIG. 10 is a graph illustrating drug delivery effects of the iontophoresis device according to an embodiment. In order to confirm the drug delivery effects, the RED battery unit was prepared in the same manner as in preparation of the RED battery unit prepared for the measurement in FIG. 6, except that the number of chamber layers was 15, and a size of the chamber was 1 cm×0.8 cm. Also, 3M clectrically conductible adhesive tape (ECAT), which is conductive fabric, was used as an intermediate unit. The first material containing unit was prepared as follows. 2.5 wt % of 2-phospho l-ascorbic acid trisodium (VCP) (available from Sigma Aldrich, US) and 3 w/v % of Carbopol 940 were dissolved in 1×PBS having pH of 7.4. By titrating with 1 M HCl and 1 M NaOH, a pH of the first material containing unit including vitamin C (VCP) was adjusted to 7. This is a stable pH at which VCP exists in the ionized form. As a thickening agent used in preparation of a dosage form, Carbopol was prepared as a sol while controlling a pH using pH indicator paper (available from GE healthcare, UK). The resultant was sufficiently stirred by using a glass rod so that a material in the first material containing unit was homogenous after each titration process. The second material containing unit was prepared in the same manner as in preparation of the first material containing unit, except that 0.9 wt % of NaCl was used instead of 2.5 wt % of VCP, and Carbopol serving as a buffer of a drug negative part was prepared as a sol. Next, in order to confirm the drug delivery effects, skin tissue was taken from a hairless mouse (Sk-hr 1, available from Hallym Experimental Animal Center). In particular, after administering euthanasia to the mouse, back skin of a site near the tail was hold by ring-shaped forceps, cut out a small portion by using scissors, and the skin and tissue membrane were disconnected by inserting the scissors inside the skin. Cutting an edge of the skin by holding the skin with hand, not with the ring-shaped forceps, and disconnecting the inside of skin and the tissue membrane were repeatedly performed, and the scissors were used close to the skin so that fat tissue or the like would not come along with the skin. The back skin of the mouse was fixed by clamps. As an experimental group (RED single), an iontophoresis device containing a drug was applid thereto. As a control group (Ctrl), an iontophoresis device containing a drug of the same concentration for the same condition was used, but the device was not activated by supplying water to the device. 3 mice were used for each of the groups. After 3 hours, washing was performed to remove the drug remaining on a surface of the skin. The skin was washed twice back and forth using 50% MeOH and 50% water for 10 seconds and then washed twice back and forth using 100% MeOH for 10 seconds. A stripping tape was attached on an outer surface of the skin, spread with ring-shaped forceps, and repeated three times to separate the stratum corneum of the skin. To analyze the drug contained in the stratum corneum (SC), three stripping tapes were collected in a conical tube, placed in 3 mL of HPLC mobile phase, and remained in a shaker for 3 hours. Next, in order to extract the drug extract in the dermis, the skin was finely cut with scissors, placed in a 15 ml conical tube, placed in 3 ml of HPLC mobile phase, and ground with a homogenizer. After performing centrifugation, the supernatant was removed and frozen. Subsequently, the remaining animal tissues were centrifuged at 1100 rpm for 5 minutes to subside, and the supernatant was centrifuged again at 15000 rpm. HPLC/LC-MS analysis was performed on the supernatant only and under the following conditions; Mobile phase: Acetonitrile/100 mmol/l Ammonium Acetate=80/20, Column: HILIC, 4.6 mm, I.D. temperature=30° C., a flow rate: 1 ml/min, a sample volume: 5 ul, detection: 254 nm. As a result, as shown in FIG. 10, in the control group, more drug remaining amount was found in the stratum corneum, whereas, in the experimental group, it was confirmed that about 40% of vitamin C, VCP, was well delivered to the skin, i.e., dermis. Therefore, it can be confirmed that the iontophoresis device according to an embodiment may deliver more drugs to the subcutaneous blood vessels through the skin.

While one or more embodiments have been described with reference to the figures, it will be understood by those of ordinary skill in the art that various changes in form and details may be made therein without departing from the spirit and scope of the disclosure as defined by the following claims.

The invention claimed is:

1. An iontophoresis device comprising:
a reversed electrodialysis (RED) battery comprising a first surface and a second surface facing each other;
an intermediate layer comprising a first intermediate layer connected to the first surface of the RED battery and a second intermediate layer connected to the second surface of the RED battery; and
a material-container connected to one surface of the intermediate layer,
wherein the RED battery comprises a plurality of chambers containing an electrolyte in form of a powder,
wherein the plurality of chambers comprise a plurality of first chambers comprising the electrolyte at a high concentration and a plurality of second chambers comprising the electrolyte at a low concentration that are disposed alternating to each other,
wherein the plurality of chambers generate a current by an ion concentration difference between the electrolyte at a high concentration and the electrolyte at a low concentration,
wherein the intermediate layer comprises a conductive material and is configured such that a current flows through the material-container when the current is generated from the RED battery,
wherein the material-container is configured such that a material in the material-container is delivered to an object by using the current generated from the RED battery,
wherein the chamber is formed of a fabric capable of absorbing an aqueous solution, and
wherein the reverse electrodialysis battery is activated when the electrolyte in form of a powder is dissolved in the aqueous solution is supplied into the chambers.

2. The iontophoresis device of claim 1, wherein the RED battery further comprises
a cation exchange membrane; and
an anion exchange membrane disposed apart from the cation exchange membrane,
wherein the plurality of chambers are at least partially defined by the cation exchange membrane and the anion exchange membrane, and
wherein a plurality of the cation exchange membranes and a plurality of the anion exchange membranes are disposed alternating to each other.

3. The iontophoresis device of claim 2, wherein a total number of the plurality of chamber is 2 to 70.

4. The iontophoresis device of claim 3, wherein the intermediate layer is connected to the cation exchange membrane or the anion exchange membrane existing on an outer surface of the RED battery.

5. The iontophoresis device of claim 1, wherein the intermediate layer is formed of conductive fabric or conductive woven.

6. The iontophoresis device of claim 2, wherein the electrolyte comprises an electrolyte paste.

7. The iontophoresis device of claim 6, wherein the electrolyte paste comprises an aqueous polymer binder.

8. The iontophoresis device of claim 1, wherein the material is contained in a first material container connected to the first intermediate layer and a second material container connected to the second intermediate layer, and wherein the material is contained in the first material container or the second material container, or in both of the first material container and the second material container.

9. The iontophoresis device of claim 1, wherein the material is comprised in hydrogel, cellulose, agaros, gelatin, or collagen.

10. The iontophoresis device of claim 1, wherein the material has a charge or a polarity.

11. The iontophoresis device of claim 1, wherein the RED battery is an only current source for delivering the material.

12. The iontophoresis device of claim 2, wherein the electrolyte is comprised in an electrolyte solution, an ion concentration of the electrolyte solution comprised in the plurality of the first chambers is in a range of about 0.1 mol/L to about 20 mol/L, and an ion concentration of the electrolyte solution comprised in the plurality of the second chambers is in a range of about 0.005 mol/L to about 10 mol/L.

13. The iontophoresis device of claim 1, wherein the iontophoresis device is a patch for delivering the material through skin.

14. The iontophoresis device of claim 2, wherein the electrolyte is selected from the group consisting of NaCl, $MgCl_2$, AgCl, $CuCl_2$, $CaCl_2$, and a combination thereof.

15. The iontophoresis device of claim 2, wherein the plurality of the first chambers and the plurality of the second chambers comprise a solid material or a hydrogel comprising the electrolyte.

16. The iontophoresis device of claim 1, wherein the fabric is fabric impregnated with the electrolyte.

17. The iontophoresis device of claim 1, wherein the material is a whitening agent, an anti-wrinkle agent, a drug, or a combination thereof.

18. The iontophoresis device of claim 17, wherein the whitening agent is a *Broussonetia kazinoki* extract, niacinamide, adenosine, arbutin, ethyl ascorbyl ether, oil soluble licorice extract, ascorbyl glucoside, ascorbyl tetraisopalmitate, magnesium ascorbyl phosphate, alpha-bisabolol, or a combination thereof; the anti-wrinkle agent is retinol, retinyl palmitate, adenosine, polyethoxylated retinamide, acetyl hexapeptide-3 or 8, acetyl octapeptide-3, acetyl tetrapeptide-5, palmitoyl pentapeptide, copper peptide, palmitoyl oligopeptide, palmitoyl dipeptide-10, palmitoyl tripeptide-1, palmitoyl tetrapeptide-7, palmitoyl pentapeptide-3, palmitoyl hexapeptide-12, pentapeptide-18 (leuphasyl), or a combination thereof; and the drug is lidocaine, ketoprofen, nicotine, caffeine, amorolfine, fentanyl, ascorbic acid, hyaluronate, argireline, or a combination thereof.

19. The iontophoresis device of claim 2, wherein a water-permeative membrane is disposed on at least one surface of the chamber, or a water supplier that supplies water to the chamber is connected to a part of at least one surface of the chamber.

20. The iontophoresis device of claim 8, wherein the first intermediate layer comprises a first surface disposed in parallel with the first surface of the RED battery and a second surface disposed in parallel with a surface of the first material-container, and
wherein the second intermediate layer comprises a first surface disposed in parallel with the second surface of the RED battery and a second surface disposed in parallel with a surface of the second material-container.

* * * * *